(12) United States Patent
Otterbeck

(10) Patent No.: US 7,547,451 B2
(45) Date of Patent: Jun. 16, 2009

(54) PELLET FORMULATION FOR THE TREATMENT OF THE INTESTINAL TRACT

(75) Inventor: Norbert Otterbeck, Uberlingen (DE)

(73) Assignee: Dr. Falk Pharma GmbH, Freiburg (DE)

( * ) Notice: Subject to any disclaimer, the term of this patent is extended or adjusted under 35 U.S.C. 154(b) by 414 days.

(21) Appl. No.: 10/360,410

(22) Filed: Feb. 7, 2003

(65) Prior Publication Data

US 2003/0133983 A1    Jul. 17, 2003

Related U.S. Application Data

(60) Division of application No. 09/906,494, filed on Jul. 16, 2001, now Pat. No. 6,551,620, which is a continuation of application No. 09/194,213, filed as application No. PCT/EP98/02319 on Apr. 20, 1998, now Pat. No. 6,277,412.

(30) Foreign Application Priority Data

Jul. 30, 1997    (DE) .................................. 197 32 903

(51) Int. Cl.
A61K 9/52    (2006.01)
A61K 9/28    (2006.01)
(52) U.S. Cl. ...................................... 424/457; 424/474
(58) Field of Classification Search ......... 424/457–462, 424/401, 474
See application file for complete search history.

(56) References Cited

U.S. PATENT DOCUMENTS

| | | | |
|---|---|---|---|
| 4,540,685 A | 9/1985 | Bauer | 514/162 |
| 4,632,921 A | 12/1986 | Bauer | 514/163 |
| 4,699,902 A | 10/1987 | Bauer | 514/163 |
| 4,863,744 A * | 9/1989 | Urquhart et al. | 424/484 |
| 5,178,866 A * | 1/1993 | Wright et al. | 424/473 |
| 5,316,772 A | 5/1994 | Jurgens, Jr. et al. | 424/472 |
| 5,505,966 A * | 4/1996 | Edman et al. | 424/493 |
| 5,541,170 A | 7/1996 | Rhodes et al. | 514/166 |
| 5,541,171 A | 7/1996 | Rhodes et al. | 514/166 |

FOREIGN PATENT DOCUMENTS

| | | |
|---|---|---|
| DE | 4236025 | 4/1994 |
| EP | 006200 | 10/1982 |
| EP | 0148811 | 7/1985 |

(Continued)

OTHER PUBLICATIONS

"Dictionary Entries: 'Mesalamine,' 'Proctosigmoiditis' and 'Inflammation'", *Stedman's Medical Dictionary*, Obtained from the Physician's Desk Reference Electronic Library on the World Wide Web at http://www.pdrel.com/>, on Dec. 17, 1999, 5 p., (1999).

(Continued)

*Primary Examiner*—San-ming Hui
(74) *Attorney, Agent, or Firm*—Schwegman, Lundberg & Woessner, P.A.

(57) ABSTRACT

An orally adminsterable pharmaceutical pellet formulation for the treatment of the intestinal tract is disclosed, which comprises a core and an enteric coating, the core including, as a pharmaceutical active compound, aminosalicylic acid or a pharmaceutically tolerable salt or a derivative thereof.

18 Claims, 2 Drawing Sheets

FOREIGN PATENT DOCUMENTS

Figure 1:
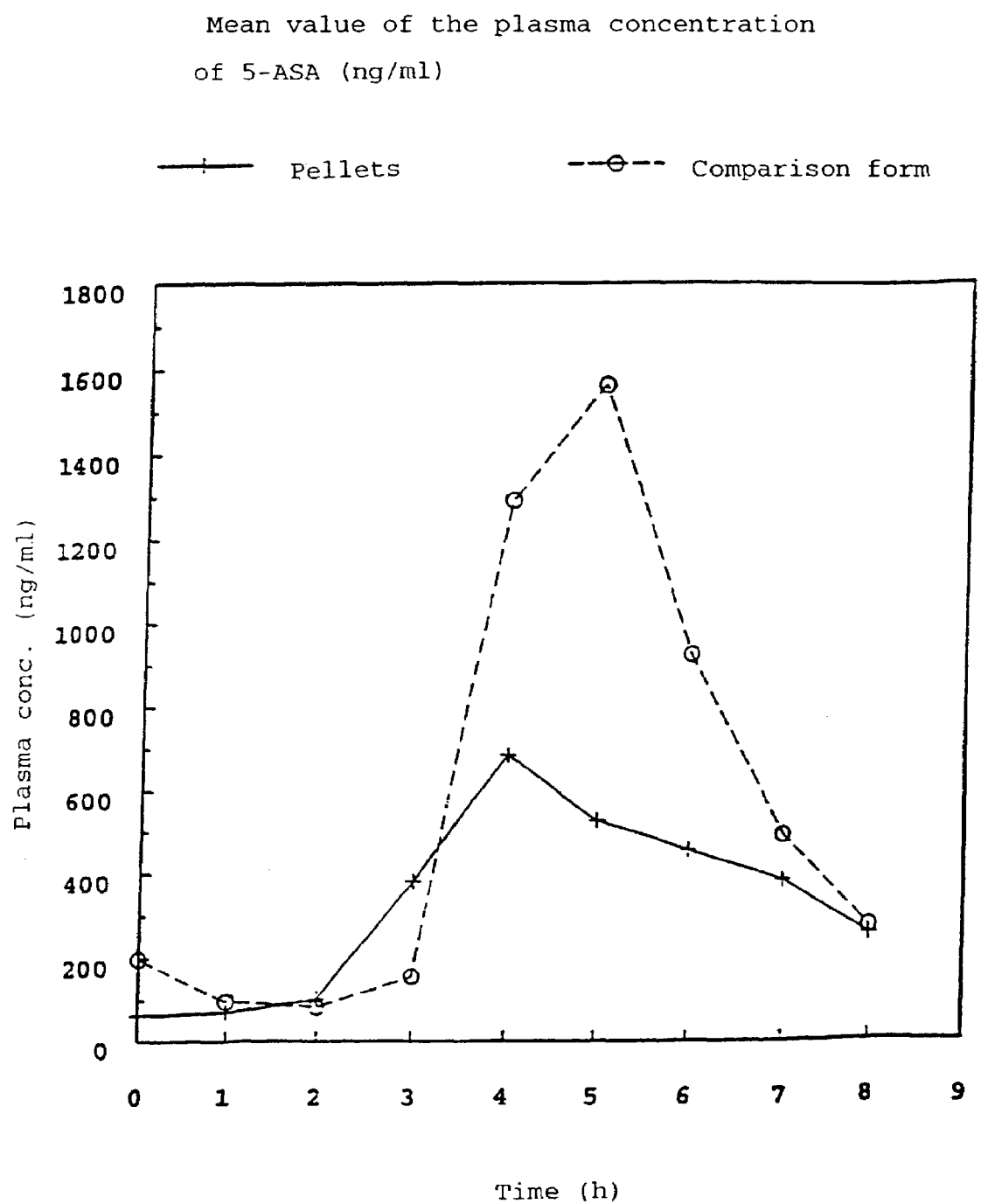

| | | |
|---|---|---|
| EP | 0248447 | 12/1987 |
| EP | 0308665 | 3/1989 |
| EP | 0453001 A1 | 10/1991 |
| EP | 0485840 A2 | 5/1992 |
| EP | 0572486 | 12/1993 |
| EP | 0595110 | 5/1994 |
| EP | 0629398 A1 | 12/1994 |
| EP | 0671168 | 9/1995 |
| EP | 0673645 | 9/1995 |
| EP | 0759303 | 2/1997 |
| FR | 2692484 | 12/1993 |
| WO | 83/00435 | 2/1983 |
| WO | 0148811 | 7/1985 |
| WO | 92/14452 | 9/1992 |
| WO | 93/07859 | 4/1993 |
| WO | 95/16451 | 6/1995 |
| WO | 95/18622 | 7/1995 |
| WO | 95/35100 | 12/1995 |
| WO | 96/04918 | 2/1996 |
| WO | 96/29058 | 9/1996 |
| WO | 96/31202 | 10/1996 |
| WO | 97/23199 | 7/1997 |

OTHER PUBLICATIONS

"Dictionary Entry: 'Pentasa Capsules' (Mesalamine/5-aminosalicylic Acid)", *Physician's Desk Reference*, Obtained from the Physician's Desk Reference Electronic Library on the World Wide Web at http://www.pdrel.com/>, on Dec. 17, 1999, 8 p., (1999).

Badawi, A.A., et al., "Drug Release From Matrices Made of Polymers With Reacting Sites", *International Journal of Pharmaceutics*, 6, 55-62, (1980).

Barry, M., "Selected side-effects: 9. Mesalazine and renal impairment", *Prescriber's Journal*, vol. 32, No. 5, pp. 205-209, (1992).

Lin, S.Y., et al., "Calcium Alginate Beads as Core Carriers of 5-Aminosalicylic Acid", *Pharmaceutical Research*, 9 (9), 1128-1131, (1992).

Watts, P.J., et al., "Encapsulation of 5-aminosalicylic Acid into Eudragit RS Microspheres and Modulation of their Release Characteristics by Use of Surfactants", *Journal of Controlled Release*, 16, 311-318, (1991).

"Data Sheets for Registration", *Rohm Brochure, Pharma Polymers*, 4 pages.

"U.S. Appl. No. 09/194,213 Final Office Action mailed Sep. 26, 2000", 7 pgs.

"U.S. Appl. No. 09/194,213 Non Final Office Action mailed Dec. 28, 1999", 7 pgs.

"U.S. Appl. No. 09/194,213 Notice of Allowance mailed Mar. 30, 2001", 5 pgs.

"U.S. Appl. No. 09/194,213 Preliminary Amendment filed Nov. 20, 1998", 2 pgs.

"U.S. Appl. No. 09/194,213 Response filed Mar. 14, 2001 to Final Office Action mailed Sep. 26, 2000", 5 pgs.

"U.S. Appl. No. 09/194,213 Response filed Jun. 28, 2000 to Non Final Office Action mailed Dec. 28, 1999", 5 pgs.

"U.S. Appl. No. 09/906,494 Non Final Office Action mailed May 6, 2002", 7 pgs.

"U.S. Appl. No. 09/906,494 Non Final Office Action mailed Sep. 25, 2001", 7 pgs.

"U.S. Appl. No. 09/906,494 Notice of Allowance mailed Nov. 4, 2002", 5 pgs.

"U.S. Appl. No. 09/906,494 Preliminary Amendment filed Jul. 18, 2001", 4 pgs.

"U.S. Appl. No. 09/906,494 Response filed Aug. 6, 2002 to Non Final Office Action mailed May 6, 2002", 7 pgs.

"U.S. Appl. No. 09/906,494 Response filed Dec. 28, 2001 to Non Final Office Action mailed Sep. 25, 2001", 7 pgs.

"U.S. Appl. No. 10/360,410, Response filed Sep. 27, 2007 to Non-Final Office Action mailed May 31, 2007", 7.

\* cited by examiner

PELLET FORMULATION FOR THE TREATMENT OF THE INTESTINAL TRACT

RELATED APPLICATIONS

This application is a Divisional of U.S. patent application Ser. No. 09/906,494, filed Jul. 16, 2001, now U.S. Pat. No. 6,551,620, which is a Continuation of Ser. No. 09/194,213, filed on Aug. 30, 1999, now U.S. Pat. No. 6,277,412, which was a filing under 35 U.S.C. 371 PCT/EP98/02319, filed on Apr. 20, 1998, which claimed priority from German Application No. 197 32 903.9, filed Jul. 30, 1997, which applications are incorporated by reference and made a part hereof.

FIELD OF THE INVENTION

The present invention relates to a pellet formulation for the treatment of the intestinal tract, which comprises, as a pharmaceutical active compound, aminosalicylic acid or a pharmaceutically tolerable salt or derivatives thereof.

BACKGROUND OF THE INVENTION

The active compound aminosalicylic acid (in particular 5-ASA) or its derivatives have been used successfully for a relatively long time for the treatment of intestinal disorders, such as, for example, ulcerative colitis and Crohn's disease (DE 31 51 196 A1).

The use of 5-ASA and its derivatives as a chemotherapeutic agent in colonic cancer is likewise known, polyps in the colon and rectum being associated with an increased risk of carcinoma (WO 95/18622).

A coloscopic polypectomy in patients with polyps in the colon and/or rectum results in a considerable reduction in risk of the formation of colonic carcinomas and is recommended as a therapy, in particular in the case of colorectal polyps. The reccurrence rate after polypectomy, however, is high and amounts to about 6-30% per year. Aminosalicylic acid is suitable for the longer-term treatment of such patients and lowers the reccurrence rate of colorectal polyps.

The action of aminosalicylic acid in the treatment of intestinal disorders, or in the prevention of their recurrence or in the prevention of secondary disorders arising therefrom and possible accompanying disorders takes place by means of the contact of the active compound directly at the site of the disorder in the intestine, the action of the aminosalicylic acid, or a derivative thereof, being directly related to its local concentration in the intestinal area to be treated.

Since inflammatory processes often affect relatively large sections of the intestinal tract, the pharmaceutical form should spread reproducibly over wide areas of the intestine and release the active compound only at the site of inflammation.

A problem in the treatment with aminosalicylic acid is that the active compound is very easily absorbed and can be excreted via the kidney before its action can occur.

In the prior art, tablets and pellets are known which are coated with an enteric coating in order to thus prevent a premature release of the active compounds.

FR-A2 692 484 discloses a tablet for the controlled release of 4-ASA in a hydrophilic matrix which consists of swellable polymers forming a gel barrier, and having an enteric coating. After dissolution of the coating, the matrix swells and forms a gel barrier through which the active compound diffuses out. After an approximately two-hour lag phase, the composition disclosed in FR-A 2 692 484 releases the active compound approximately linearly in the intestine over a period of time of a further 14 h.

EP 0 453 001 A1 discloses a pharmaceutical composition in which the active compound is covered with at least two membranes, of which one is soluble at a pH of $\geq 5.5$ and the other is insoluble at this pH but is permeable to the intestinal fluids.

EP 0 148 811 A1 discloses a pharmaceutical composition which consists of a core which contains the active compound. The core is surrounded by two layers, of which the inner layer is a diffusion membrane and the second layer is an anionic polymer and/or a fatty acid having a $pK_a$ of 4.5 to 7.

EP 0 629 398 A1 discloses pharmaceutical compositions in which the active compound-containing core is surrounded by an enteric phase. According to Example 2, the core can contain small amounts of hydroxypropylcellulose. The active compound should be released rapidly after dissolution of the enteric phase.

EP 0 485 840 A2 discloses an oral pharmaceutical form which contains a shell material surrounding the active compound consisting of a polysaccharide and a film-forming polymer material.

A disadvantage in the case of the pharmaceutical formulations known in the prior art is that the active compound is also absorbed into the blood circulation. This amount of active compound is thus lacking in the intestine, so that the effective dose of the medicament is reduced by the part of the active compound which is found in the blood.

Moreover, patients who suffer from intestinal disorders frequently have to be further treated over relatively long periods with the active compound, or derivatives thereof, after the acute disorder has died down in order to prevent the disorder flaring up again or secondary disorders resulting from the original disorder. In the case of such a long-term treatment, however, it has proven to be a problem that a certain nephrotoxicity of systemically available 5-ASA, i.e. 5-ASA found in the bloodstream, or derivatives thereof cannot be excluded (M. Barry, Prescribers Journal, 1992, 32, 205).

It is thus an object of the present invention to make available an orally administrable pharmaceutical formulation which does not have these disadvantages. According to the invention, formulations are therefore made available which have a controlled release profile which results in a high local active compound concentration at the site of action and simultaneously guarantees a blood level of the active compound which is as low as possible.

In the context of the present invention, it has now been found that pellet formulations are particularly suitable for this purpose, since unlike a tablet they spread the pharmaceutical form reproducibly over wide areas of the intestine and are thus particularly suitable for treatment of inflammatory processes, which often affect relatively large sections of the intestinal tract. In order to achieve the necessary local active compound concentration, the active compound must in this case be released at the site of inflammation within a relatively short time (up to a few hours) without, however, it being released virtually immediately, in order that its action does not wear off too rapidly.

The use of a swellable, gel-forming matrix such as described in FR-A 2 692 484 is not suitable for pellets having a diameter of $\leq 3$ mm, since on account of the small diameter the polymer is very rapidly penetrated by the water, eroded as a result, and the active compound would thus be released virtually immediately (about 30 min).

In the context of the present invention, however, it has surprisingly been found that, if the active compound is present in the pellet core in a non gel-forming polymer matrix which is essentially insoluble and permeable to intestinal fluids and the active compound, a markedly reduced release of the active compound into the blood, with simultaneously increased local concentration of the active compound at the site of the disorder in the intestine, is guaranteed in comparison with aminosalicylic acid formulations already known in the prior art.

The present invention thus relates to an orally administrable pharmaceutical pellet formulation having a controlled release profile for the treatment of the intestinal tract, which comprises a core and an enteric coating, and, if appropriate, further pharmaceutically tolerable additives, the core including as a pharmaceutically active compound aminosalicylic acid or a pharmaceutically tolerable salt or derivative thereof, wherein the active compound is present in the core in a non gel-forming polymer matrix which is essentially insoluble in the intestinal tract and permeable to intestinal fluids and the active compound, the matrix-forming polymer making up at least 1% by weight of the total weight of the core.

The invention furthermore relates to a process for the production of the pellets described above and their use for the production of a medicament for the treatment of intestinal disorders, such as inflammatory intestinal disorders, preferably in the active phase and/or in the remission phase, for the prevention of these disorders, for the prevention of the recurrrence of these disorders or secondary disorders resulting therefrom, and of possible accompanying disorders and also for the treatment of intestinal cancer. The medicament is particularly suitable for the treatment of inflammatory intestinal disorders such as Crohn's disease and ulcerative colitis, and for the prevention, treatment and/or prevention of the reformation of polyps in the gastrointestinal tract. Moreover, the medicament is suitable for the prevention of colorectal carcinomas in patients with adenomas and/or polypous growth, in particular with polypous growth in the intestine. The medicament is moreover used for lowering the recurrence rate of colorectal polyps.

Preferred active compounds are 5-aminosalicylic acid (also called mesalazine), 4-aminosalicylic acid and, serving as a prodrug for 5-ASA, 2-hydroxy-5-phenylazobenzoic acid derivatives such as sulfasalazine (5-[4-(2-pyridylsulfamoyl)phenylazo]salicylic acid) and balsalazide (the sodium salt of the azo derivative of 4-aminobenzoyl-β-alanine and 5-aminosalicylic acid). 5-ASA is particularly preferred.

In addition to the active compound, the pellet core comprises 1% by weight, based on the total weight of the core, of a matrix-forming, non gel-forming polymer which is essentially insoluble in the intestinal tract and permeable to intestinal fluids and the active compound. Suitable matrix-forming polymers are, for example, those polymers which are known in the prior art as coating lacquers for delayed-release pharmaceuticals, such as, for example, (meth)acrylic ester copolymers.

Among the polymers which are essentially insoluble in the intestinal tract and permeable to intestinal fluids and the active compound, those are preferred which are insoluble or particularly preferably water-insoluble in the intestinal tract.

Methyl acrylate copolymers and ammoniomethacrylate copolymers of the type such as can be obtained under the tradename Eudragit® RS/RL/NE are particularly preferred. As functional groups, these polymers have ester groups (Eudragit® NE) or ammonium groups (Eudragit® RL/RS). Poly(ethyl acrylate, methyl methacrylate) and poly(ethyl acrylate, methyl methacrylate, trimethylammonioethyl methacrylate chloride) are preferred. These polymers are obtainable, for example, as poly(ethyl acrylate, methyl methacrylate) 2:1 in 40% strength aqueous dispersion as Eudragit® NE 40 D and as poly(ethyl acrylate, methyl methacrylate, trimethylammonioethyl methacrylate chloride) 1:2:0.1 in 12.5% strength isopropanolic solution as Eudragit® RS 12.5 and in the composition 1:2:0.2 as Eudragit® RL 12.5. The most preferred is Eudragit® NE 40 D.

The polymer must be present in an amount which is sufficient to form a matrix for the active compound and which guarantees a delayed release of the active compound. For this purpose, an amount of at least 1% by weight, preferably at least 4% by weight, based on the total weight of the core, has proven suitable. Larger amounts of, for example, approximately 21% by weight can also be employed. 4% by weight to 10% by weight is preferably employed.

The active compound is preferably homogeneously dispersed in the matrix described above and is released with a delay after dissolving the enteric coating. The matrix with the active compound homogeneously dispersed therein advantageously extends through the entire core.

The enteric coating should only dissolve after the formulation has left the stomach. Necessary coatings for this purpose are disclosed in the prior art (e.g. EP 0 453 001 A1).

Preferred enteric coatings according to the invention comprise a methacrylic acid copolymer or methylhydroxypropylcellulose phthalate. Poly(methacrylic acid, methyl methacrylates), which are obtainable under the tradenames Eudragit® L or S and have free carboxyl groups as functional groups, are preferred. These polymers are insoluble in the gastric juice, but dissolve in digestive juices above pH 5.5-7 depending on the number of functional carboxyl groups. Poly(methacrylic acid, methyl methacrylate) 1:1 (Eudragit® L 100; methacrylic acid copolymer, USP/NF type A) and poly(methacrylic acid, methyl methacrylate) 1:2 (Eudragit® S; methacrylic acid copolymer, USP/NF type B) are particularly preferred. Eudragit® L 100 is the most preferred. Mixtures of the coating materials mentioned, in particular of Eudragit® L and Eudragit® S, can also be used.

The pellet formulation can comprise one or more coatings, however pellet formulations in which the pellet only comprises one coating are preferred.

Both the core and the coating of the pellet formulation according to the invention can include one or more of the abovementioned matrix or coating materials.

The pellet formulations according to the invention can additionally contain further pharmaceutically tolerable additives both in the core and in the coating. Examples of pharmaceutically tolerable additives include polyvinylpyrrolidone, microcrystalline cellulose, silica, magnesium stearate, lactose, cornstarch, triethyl citrate, talc, titanium dioxide and polyethylene glycol.

A particularly preferred pellet formulation according to the present invention comprises 5-ASA as an active compound in the core in a poly(ethyl acrylate, methyl methacrylate) 2:1 matrix, the polymer containing ester groups as functional groups, and an enteric coating which contains poly(methacrylic acid, methyl methacrylate) 1:1 or 1:2 with free carboxyl groups as functional groups, and, if appropriate, further pharmaceutically tolerable additives.

Moreover, a mixture of Eudragit® S and Eudragit® L, preferably approximately 1:1, is advantageously employed in a coating for the pellet formulations according to the invention.

The pellet formulation according to the invention is distinguished by a controlled release profile. Preferably, the release of active compound in 0.1 M HCl after 2 h is <10%, in particular <5%, and in artificial gastric juice at pH 6.8 after 0.5 h 10-30%, in particular 10-20%, after 2 h 40-60%, in particular 40-50%, and after 6 h at least 80%, in particular at least 85%.

The pellet formulations according to the invention can be prepared according to conventional processes known to the person skilled in the art. For example, the matrix material is first mixed with the active compound and, if appropriate, the further pharmaceutically tolerable additives and shaped to give pellets. The coating is then applied, e.g. sprayed on, in the form of a lacquer suspension in a suitable suspending agent such as ethanol and/or water. The pellets can in this case have a size of 0.1-3 mm, preferably 0.5-1 mm, and are combined in unit dose forms such as tablets or capsules for the production of a medicament. The present invention therefore also relates to pharmaceutical formulations which comprise the pellets according to the invention, in particular gelatin capsules which contain the pellets according to the invention.

On oral administration, the pellet formulations thus obtained result, in comparison with other preparations with the same active compound, in lower active compound concentrations in the blood with a simultaneously higher concentration of the active compounds in the intestine, as a result of which the side effect potential caused by the systemically available active compound or its metabolites, is markedly reduced.

The pellet formulation according to the invention is thus particularly suitable for the treatment of intestinal conditions in which a relatively long-term administration of the active compound is indicated, such as inflammatory intestinal disorders in their active phase and their remission phase, in the prevention of adenomas and/or polyp formation, in the prevention of the recurrence of adenomas and/or polyps and in the prevention of secondary disorders resulting therefrom and possible accompanying disorders.

Figure 2:
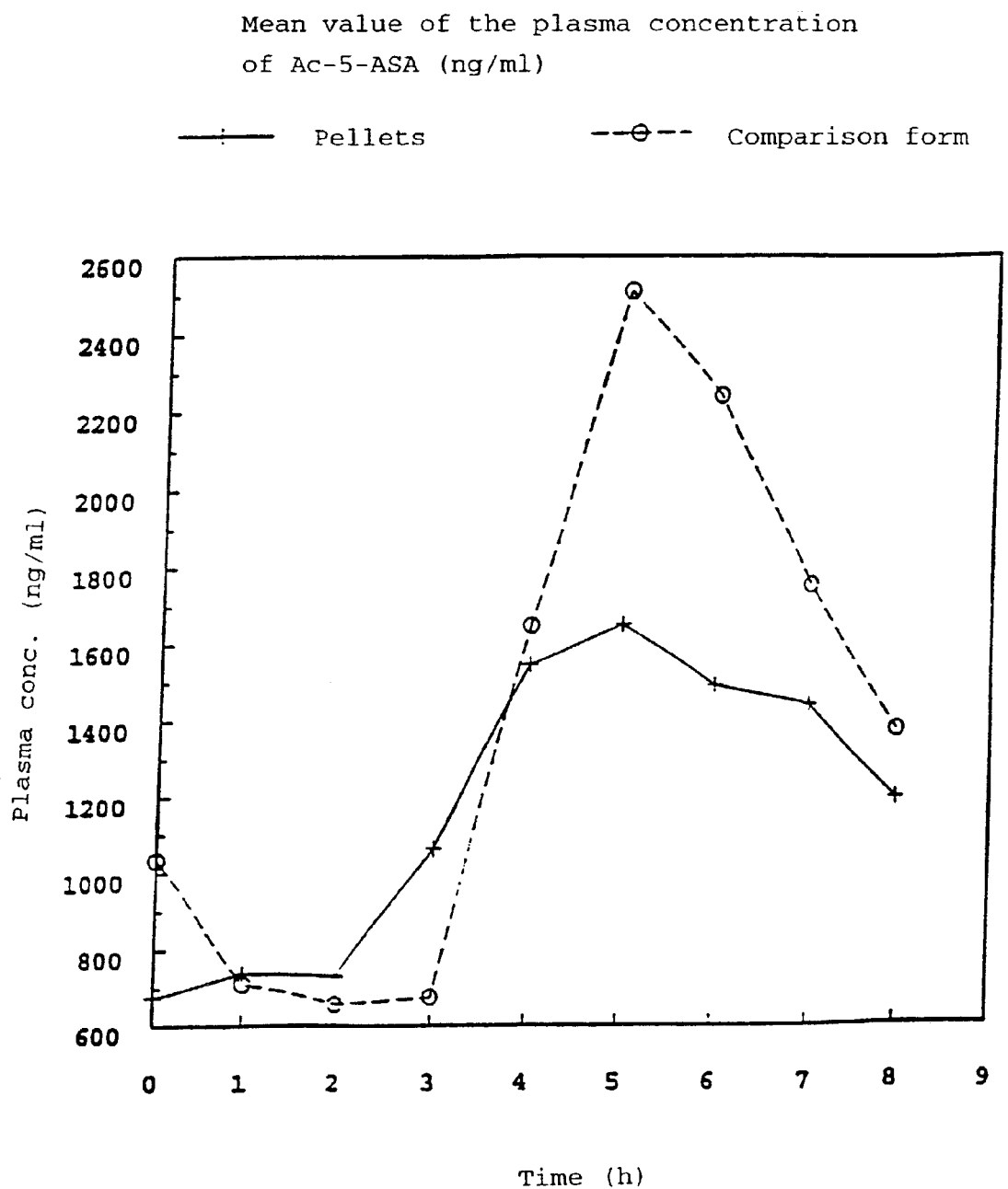

FIGS. 1 and 2 show graphs of the plasma concentrations of 5-ASA (FIG. 1) and Ac-5-ASA (FIG. 2) against time.

The following examples serve to illustrate the invention.

Example 1 describes two different pellet cores (Example 1.1-1.2) and four different pellet coatings (Example 1.a-1.d). The different cores can be combined in any desired manner with the different coatings, the pellet core from Example 1.1 together with the coating from Example 1.a being a particularly preferred example.

EXAMPLE 1

Examples of pellet cores:

1.1

| I | Mesalazine | 5000 g |
|---|---|---|
| II | Cellulose, microcrystalline | 1500 g |
| III | Hydroxypropylmethylcellulose | 200 g |
| IV | Silica | 25 g |
| V | Poly (ethyl acrylate, methyl methacrylate) 2:1 as a 40% strength aqueous dispersion, tradename Eudragit ® NE 40 D | 750 g |
| VI | Magnesium stearate | 250 g |

I-IV are mixed, moistened with V and intensively kneaded. VI is finally scattered in. The moist mass is pressed through an extruder with a die bore of 1 mm. The extruded pellets are cut into pieces about 1 mm long and rounded in a spheronizer. The pellets are dried at 60° C.

1.2

| I | Mesalazine | 5000 g |
|---|---|---|
| II | Cellulose, microcrystalline | 1500 g |
| III | Hydroxypropylmethylcellulose | 200 g |
| IV | Silica | 25 g |
| V | Poly (ethyl acrylate, methyl methacrylate, trimethylammonioethyl methacrylate chloride) 1:2:0.1; as a 12.5% strength isopropanolic solution; tradename Eudragit ® RS 12.5 | 2500 g |
| VI | Magnesium stearate | 250 g |

I-IV are mixed, moistened with V and intensively kneaded. VI is finally scattered in. The moist mass is pressed through an extruder with a die bore of 1 mm. The extruded pellets are cut into pieces about 1 mm long and rounded in a spheronizer. The pellets are dried at 60° C.

Examples of Pellet Coatings

Formulations for 5000 g pellets, corresponding to Examples 1.1-1.2

1.a

| I | Poly (methacrylic acid, methyl methacrylate) 1:1; tradename Eudragit ® L 100; (methacrylic acid copolymer, USP/NF type A) | 750 g |
|---|---|---|
| II | Triethyl citrate | 75 g |
| III | Talc | 200 g |
| IV | Titanium dioxide | 125 g |
| V | Magnesium stearate | 50 g |

I is dissolved in 7000 g of an ethanol/water mixture (8:2). II-V are suspended in the solution; the lacquer suspension is sprayed on at a feed air temperature of 40° C. in a suitable apparatus.

1.b

| I | Poly (methacrylic acid, methyl methacrylate) 1:2; tradename Eudragit ® S; (methacrylic acid copolymer, USP/NF type B) | 350 g |
|---|---|---|
| II | Triethyl citrate | 35 g |
| III | Talc | 100 g |
| IV | Titanium dioxide | 125 g |
| V | Magnesium stearate | 50 g |

I is dissolved in 3500 g of an ethanol/water mixture (8:2). II-V are suspended in the solution; the lacquer suspension is sprayed on at a feed air temperature of 40° C. in a suitable apparatus.

1.c

| I | Poly (methacrylic acid, methyl methacrylate) 1:2; tradename Eudragit ® S; (methacrylic acid copolymer, USP/NF type B); poly (methacrylic acid, methyl methacrylate) 1:1; tradename Eudragit ® L 100; (methacrylic acid copolymer, USP/NF type A) (mixed in the ratio 1.1:1) | 420 g |
|---|---|---|
| II | Triethyl citrate | 75 g |
| III | Talc | 200 g |

-continued

| | | |
|---|---|---|
| IV | Titanium dioxide | 125 g |
| V | Magnesium stearate | 50 g |

I is dissolved in 5000 g of an ethanol/water mixture (8:2). II-V are suspended in the solution; the lacquer suspension is sprayed on at a feed air temperature of 40° C. in a suitable apparatus.

1.d

| | | |
|---|---|---|
| I | Methylhydroxypropylcellulose phthalate | 410 g |
| II | Ethylcellulose | 44 g |
| III | Polyethylene glycol 6000 | 40 g |
| IV | Talc | 200 g |
| V | Titanium dioxide | 125 g |
| VI | Magnesium stearate | 50 g |

I and II are dissolved in 5000 g of an ethanol/water mixture (9:1). III-VI are suspended in the solution; the lacquer suspension is sprayed on at a feed air temperature of 40° C. in a suitable apparatus.

EXAMPLE 2

To determine the release of the active compound from the pellets according to the invention, the "basket" method was used. The stirrer speed was 100 rpm and the temperature was kept constant at 37° C. 0.1 M HCl according to USP was used as artificial gastric juice and USP phosphate buffer (pH 6.8) as artificial intestinal juice.

Table 1 indicates the active compound release of the pellet formulation according to the invention having a core according to Example 1.1 and a coating according to Example 1.a under the above-mentioned conditions.

TABLE 1

| pH | Time [min] | Release [%] |
|---|---|---|
| 1.2 | 120 | 1.6 |
| 6.8 | 30 | 12.2 |
| | 60 | 24.9 |
| | 90 | 36.0 |
| | 120 | 45.2 |
| | 150 | 53.0 |
| | 180 | 59.7 |
| | 240 | 70.6 |
| | 300 | 78.8 |
| | 360 | 85.4 |

EXAMPLE 3

In order to obtain results about the active compound absorption into the blood after administration of the pellet formulation according to the invention, the plasma concentrations of 5-ASA and acetyl-5-ASA (As-5-ASA), its degradation product, were investigated in a time-dependent manner. In a cross-over arrangement, 24 healthy subjects received 500 mg of 5-ASA in two different pharmaceutical formulations (pellets according to the invention having a core according to Example 1.1 and coating according to Example 1.a and commercially available Salofalk® tablets (mesalazine in the form of enteric tablets) as a comparison preparation) over a period of 4 days (3×500 mg of 5-ASA daily). To determine the plasma concentration of 5-ASA and acetyl-5-ASA, venous blood samples were taken from the subjects.

Tab. 2 shows the plasma concentration of 5-ASA and Ac-5-ASA averaged from 24 patients under steady-state conditions.

TABLE 2

Plasma concentration of 5-ASA and Ac-5-ASA in 24 subjects [ng/ml] (mean value)

| Time after administration [h] | Pellets | | Comparison preparation | |
|---|---|---|---|---|
| | [5-ASA] | [Ac-5-ASA] | [5-ASA] | [Ac-5-ASA] |
| 0 | 63.49 | 676.35 | 198.42 | 1033.89 |
| 1 | 71.50 | 739.46 | 96.66 | 711.70 |
| 2 | 102.97 | 731.34 | 82.86 | 657.16 |
| 3 | 382.02 | 1063.59 | 156.55 | 675.83 |
| 4 | 686.03 | 1549.00 | 1293.30 | 1651.01 |
| 5 | 527.39 | 1653.73 | 1564.33 | 2511.99 |
| 6 | 456.70 | 1493.00 | 924.75 | 2243.11 |
| 7 | 384.25 | 1442.96 | 492.91 | 1755.05 |
| 8 | 257.16 | 1196.51 | 275.11 | 1377.46 |

It is evident from Table 2 and from FIGS. 1 and 2 that markedly lower plasma levels can be achieved both from 5-ASA and from its metabolite Ac-5-ASA if 5-ASA administered to the subjects in the form of the pellet formulation according to the invention. This result is confirmed by the average $C_{max}$ values (average of the $C_{max}$ values calculated from the data of the individual subjects). In the case of the comparison formulation, the average $C_{max}$ value was 2001 ng/ml for 5-ASA and 2617 ng/ml for Ac-5-ASA while in the case of the pellet formulation according to the invention the average $C_{max}$ value was 755 ng/ml for 5-ASA and 1810 ng/ml for Ac-5-ASA. The average $C_{max}$ value of the pellet formulation is thus only 37.7% of the average $C_{max}$ value of the comparison formulation for 5-ASA and only 69% for Ac-5-ASA.

EXAMPLE 4

In order to confirm an increased local release of the 5-ASA in the intestine, feces samples of 4 subjects who had received 1500 mg of 5-ASA were investigated for 5-ASA and Ac-5-ASA in a further investigation. To this end, the feces of the subjects were collected for 71 hours and investigated for free 5-ASA and Ac-5-ASA which were not bound in the pellet or in the comparison formulation (Tab. 3). The pellets according to the invention employed were those having a core according to Example 1.1 and a coating according to Example 1.a; the comparison preparation used was commercially available Salofalk® tablets (mesalazine in the form of enteric tablets).

TABLE 3

Cumulative fecal excretion of 5-ASA and 5-Ac-ASA of 4 subjects [mg] (mean value)

| Pellets | | Comparison preparation | |
|---|---|---|---|
| [5-ASA] | [Ac-5-ASA] | [5-ASA] | [Ac-5-ASA] |
| 287.5 | 367.9 | 222.9 | 275.7 |

It is evident from the table that both the amount of the 5-ASA released in the intestine by the pellet formulation according to the invention, at 287.5 mg, and the amount of free Ac-5-ASA, at 367.9 mg, is higher by 29% or 44% respectively than in the comparison formulation. Since Ac-5-ASA can only be formed in the intestine by the interaction with the intestinal mucous membrane, the increased amount of Ac-5-ASA in the pellet formulation shows that markedly more active compound comes into contact with the intestinal mucous membrane and can thus display its curative action than in the comparison formulation.

These investigations confirm that the concentration of the active compound 5-ASA or its degradation product Ac-5-ASA in the blood can be significantly lowered by the pellet formulation according to the invention in comparison with commercially available 5-ASA preparations and thus the danger of possible side effects (nephrotoxicity etc.) is also lower. As a result of the reduced absorption of the active compound into the blood, markedly higher amounts of the active compound are available in the intestine. These also come into contact with the intestinal mucous membrane and can display their action there, as the amounts of Ac-5-ASA, which are higher in comparison with the comparison formulation and which are formed in the intestine by the direct contact of 5-ASA with the intestinal mucous membrane, confirm. Unlike the systemically available 5-ASA and Ac-5-ASA, the 5-ASA and AC-5-ASA present in the intestine cannot have a nephrotoxic action, since it is not excreted via the kidney, but with the feces.

Thus the pellet formulation according to the invention is preferably suitable for intestinal conditions in which a relatively long-term administration of the active compound is indicated, such as inflammatory intestinal disorders in their active phase and in their remission phase, in the prevention of polyp formation, in the prevention of the recurrence of polyps and in the prevention of secondary disorders resulting therefrom and possible accompanying disorders.

The invention claimed is:

1. A process for preparing an orally administrable pharmaceutical pellet formulation having a controlled release profile for the treatment of the intestinal tract, which pellet comprises a core including an aminosalicyclic acid as a pharmaceutically active compound or a pharmaceutically acceptable salt thereof and optionally pharmaceutically tolerable additives, wherein the active compound is present in the core in a non gel-forming polymer matrix which matrix is essentially insoluble in the intestinal tract and permeable to intestinal fluids and the active compound, the matrix-forming polymer making up at least 1% by weight of the total weight of the core, wherein the process comprises:
mixing the active compound and the non gel-forming polymer matrix;
scattering in a pharmaceutically tolerable additive; and
extruding a moist mass of the matrix-forming polymer and the active compound.

2. The process of claim 1, wherein the matrix-forming polymer comprises co-poly(ethyl acrylate, methyl methacrylate) or ter-poly(ethyl acrylate, methyl methacrylate, trimethylammonioethyl methacrylate chloride).

3. The process of claim 1 or 2, wherein the matrix-forming polymer comprises 4 to 10% by weight of the total weight of the core.

4. The process of claim 1, wherein the aminosalicyclic acid comprises 5-aminosalicyclic acid.

5. The process of claim 1, further comprising applying an enteric coating to a pellet formed from the moist mass.

6. The process of claim 5, wherein the enteric coating comprises a methacrylic acid containing copolymer or methylhydroxypropyl cellulose phthalate.

7. The process of claim 6, wherein the methacrylic acid containing copolymer comprises co-poly(methacrylic acid, methyl methacrylate), wherein the co-polymer comprises free carboxylic acid functional groups.

8. A process for preparing an orally administrable pharmaceutical pellet formulation having a controlled release profile, which pellet comprises a core comprising 5-aminosalicylic acid (5-ASA) or a pharmaceutically acceptable salt thereof, wherein the 5-ASA is present in the core in a non gel-forming polymer matrix, wherein the matrix is essentially insoluble in the intestinal tract and permeable to intestinal fluids, the process comprises:
mixing the 5-ASA and the non gel-forming polymer matrix;
scattering in magnesium sterate; and
extruding a moist mass.

9. The process of claim 8, further comprising applying an enteric coating to a pellet formed from the moist mass.

10. The process of claim 9, wherein the enteric coating comprises a methacrylic acid containing copolymer or methylhydroxypropyl cellulose phthalate.

11. The process of claim 10, wherein the methacrylic acid containing copolymer comprises co-poly(methacrylic acid, methyl methacrylate), wherein the co-polymer comprises free carboxylic acid functional groups.

12. The process of claims 1 or 8, further comprising cutting the moist mass into pieces.

13. The process of claim 12, wherein the pieces are about 1 mm long.

14. The process of claim 12, further comprising rounding the pieces in a spheronizer.

15. The process of claim 14, further comprising drying the pieces.

16. The process of claim 15, wherein the pieced are dried at about 60° C.

17. The process of claim 15, further comprising:
dissolving poly(methacrylic acid, methylmethacrylate) 1:1 in an ethanol/water mixture;
suspending triethyl citrate, talc, titanium dioxide and magnesium state in the mixture; and
coating the pieces with the suspended mixture.

18. The process of any of claims 7, 8, 9, 10, or 11, further comprising applying a single coating layer to a pellet formed from the moist mass.

* * * * *